United States Patent

Eder

[11] Patent Number: 6,063,070
[45] Date of Patent: May 16, 2000

[54] DETACHABLE ANEURYSM NECK BRIDGE (II)

[75] Inventor: Joseph C. Eder, Los Altos Hills, Calif.

[73] Assignee: Target Therapeutics, Inc., Fremont, Calif.

[21] Appl. No.: 09/126,700

[22] Filed: Jul. 30, 1998

Related U.S. Application Data

[60] Provisional application No. 60/054,768, Aug. 5, 1997.

[51] Int. Cl.$^7$ .................................................. A61B 17/03
[52] U.S. Cl. ............................................. 606/1; 606/213
[58] Field of Search ................................ 606/1, 191, 200, 606/213, 108, 198; 604/104; 623/1, 11, 12

[56] References Cited

U.S. PATENT DOCUMENTS

| | | |
|---|---|---|
| 3,174,851 | 3/1965 | Buehler et al. . |
| 3,351,463 | 11/1967 | Rozner et al. . |
| 3,753,700 | 8/1973 | Harrison et al. . |
| 4,643,184 | 2/1987 | Mobin-Uddin . |
| 4,710,192 | 12/1987 | Liotta et al. . |
| 4,739,768 | 4/1988 | Engelson . |
| 4,994,069 | 2/1991 | Ritchart et al. . |
| 5,108,407 | 4/1992 | Geremia et al. ........................ 606/108 |
| 5,122,136 | 6/1992 | Guglielmi et al. . |
| 5,226,911 | 7/1993 | Chee et al. . |
| 5,250,071 | 10/1993 | Palermo . |
| 5,261,916 | 11/1993 | Engelson . |
| 5,354,295 | 10/1994 | Guglielmi et al. . |
| 5,421,832 | 6/1995 | Lefebvre .................................... 604/53 |
| 5,509,900 | 4/1996 | Kirkman ................................... 604/104 |
| 5,624,449 | 4/1997 | Pham et al. . |
| 5,733,294 | 3/1998 | Forber et al. .......................... 606/151 |
| 5,980,554 | 11/1999 | Lenker et al. . |

FOREIGN PATENT DOCUMENTS

| | | |
|---|---|---|
| 2 641 692 | 7/1990 | France . |
| 233 303 A1 | 2/1986 | Germany . |
| 94 13 645 U | 12/1994 | Germany . |
| WO 97/26939 | 7/1997 | WIPO . |

*Primary Examiner*—Linda C. M. Dvorak
*Assistant Examiner*—Roy Gibson
*Attorney, Agent, or Firm*—Morrison & Foerster LLP

[57] ABSTRACT

This is a device for bridging the neck of either a wide-necked or narrow-necked aneurysm in the vasculature and stabilizing the presence of vaso-occlusive devices (such as helically wound coils) in that aneurysm. The retainer assembly may be delivered from its attachment to the distal end of a tubular member preferably by the severance of by an included electrolytically severable joint. The retainer assembly itself typically has a number of array elements which are intended to be resident within the aneurysm after the device is deployed from the distal end of a catheter. After deployment of this retainer, the aneurysm is at least partially filled with a vaso-occlusive device such as helically wound coils.

14 Claims, 7 Drawing Sheets

DETACHABLE ANEURYSM NECK BRIDGE (II)

CROSS REFERENCE TO RELATED APPLICATION

This application is a conversion to regular U.S. patent application of provisional U.S. application Ser. No. 60/054,768 filed Aug. 5, 1997.

FIELD OF THE INVENTION

This invention is a device for bridging the neck of either a wide-necked or narrow-necked aneurysm in the vasculature and stabilizing the presence of vaso-occlusive devices (such as helically wound coils) in that aneurysm. The retainer assembly may be delivered from its attachment to the distal end of a tubular member preferably by the severance of by an included electrolytically severable joint. The retainer assembly itself typically has a number of array elements which are intended to be resident within the aneurysm after the device is deployed from the distal end of a catheter. After deployment of this retainer, the aneurysm is at least partially filled with a vaso-occlusive device such as helically wound coils.

BACKGROUND OF THE INVENTION

Different implantable medical devices have been developed for treating a number of ailments associated with body lumens. In particular, occlusive devices are useful in filling vascular or other body spaces. Some body spaces, such as vascular aneurysms, are formed due to a weakening in the wall of an artery. Often these aneurysms are the site of internal bleeding and stroke. A variety of different embolic agents are known as, at least arguably, suitable for treatment of these anomalies. These treatments are commonly known as "artificial vaso-occlusion."

One such class of embolic agents includes indictable fluids or suspensions, such as microfibrillar collagen, various polymeric beads, and polyvinylalcohol foam. These polymeric agents may additionally be crosslinked, sometimes in vivo, to extend the persistence of the agent at the vascular site. These agents are often introduced into the vasculature through a catheter. After such introduction, the introduced materials there form a solid space-filling mass. Although some provide excellent short term occlusion, many are thought to allow vessel recanalization due to absorption of polymer into the blood. Another procedure in which a partially hydrolyzed polyvinylacetate (PVA) is dissolved in an ethanol solvent and ejected into a desired vascular site is found in Park et al. (attorney docket no. 29025-20112.00) U.S. patent application Ser. No. 08/734,442 filed Oct. 17, 1996 for "LIQUID LMBOLIC AGENTS". Other materials such as hog hair and suspensions of metal particles have also been suggested and used by those wishing to form occlusions.

Other materials including polymer resins, typically cyanoacrylates, are also employed as injectable vaso-occlusive materials. These resins are typically mixed with a radio-opaque contrast material or are made radio-opaque by the addition of a tantalum powder. Their use is fraught with problems in that placement of the mixture is quite difficult. These materials may crosslink with the human body. Inadvertent embolisms in normal vasculature (due to the inability of controlling the destination of the resins) is not uncommon. The material is also difficult or impossible to retrieve once it has been placed in the vasculature.

Over the past few years, advancements in the artificial occlusion of vessels and aneurysms have included the delivery and implantation of metal coils as vaso-occlusive devices. Implantable metal coils that are useful as artificial occlusion devices in vasculature lumens or aneurysms are herein referred to as "vaso-occlusions coils."

Vaso-occlusion coils are generally constructed of a wire, usually made of a metal or metal alloy, that is wound to a helix. Many such devices are introduced to the selected target site through a catheter in a stretched linear form. The vaso-occlusive device assumes an irregular shape upon discharge of the device from the distal end of the catheter a variety of vaso-occlusive coils and braids are known. For instance, U.S. Pat. No. 4, 994,069, to Ritchart et al. shows a flexible, preferably coiled, wire for use in small vessel vaso-occlusion. Unlike vaso-occlusive coils used prior to that time, Ritchart et al taught a coil which is fairly soft and is delivered to the site using a pusher within a catheter lumen. Upon discharge from the delivery catheter, the coil may undertake any of the number of random or regular configurations used to fill the site. The coils may be used for small vessel sites, e.g., 0.5–6 mm in diameter. The coils themselves are described as being between 0.010 and 0.030 inches in diameter. The length of the coil wire is typically 15 to 20 times the diameter of the vessel to be occluded. The wire used to make up the coils may be, for instance, 0.002 to 0.006 inches in diameter. Tungsten, platinum, and gold threads or wires are said to be preferred. These coils have a variety of benefits including the fact that they arc relatively permanent, they may be easily imaged radiographically, they may be located at a well defined vessel site, and they can be retrieved.

It is common that these vaso-occlusive devices be delivered through micro atheters such as the type disclosed in U.S. Pat. No. 4,739,768, to Engelson. These microcatheters track a guidewire to a point just proximal or within the desired site for occlusion. The coil is advanced through the microcatheter (once the guidewire is removed) and out the distal end hole so to at least partially fill the selected space and create an occlusion.

In addition to vaso-occlusion devices or coils having predetermined secondary shapes that dictate in part their space filling mechanism, other vaso-occlusive coils have been disclosed that take on random shapes when expelled from a delivery sheath. One such type is a vaso-occlusive coil often referred to as "a liquid coil". One example of such a vaso-occlusive coil is disclosed in pending U.S. patent application Ser. No. 08/413,970, filed Mar. 30, 1995. This describes a very soft and flexible coil which is flow-injectable through a delivery catheter using, e.g., saline solution.

In addition to the various types of space filling mechanisms and geometries of vaso-occlusive coils, other particularized features of coil designs, such as mechanisms for delivering vaso-occlusive coils through delivery catheters and implanting them in a desired occlusion site, have also been described. The examples of categories of vaso-occlusive coils based upon their delivery mechanisms include pushable coils, mechanically detachable coils, and electrolytically detachable coils.

One example of the type of vaso-occlusive coil referred to above as the "pushable coil" is disclosed in Ritchart et al., discussed above. Pushable coils are commonly provided in a cartridge and are pushed or "plunged" from the cartridge into a delivery catheter lumen pusher advances the pushable coil through and out of the delivery catheter lumen and into the site for occlusion.

Mechanically detachable vaso-occlusive devices are typically integrated with a pusher rod and are mechanically detached from the distal end of that pusher after exiting a delivery catheter. Examples of such mechanically detachable vaso-occlusive coils are found in U.S. Pat. No. 5,261,916 to Engelson or U.S. Pat. No. 5,250,071 to Palermo.

Finally, examples of electrolytically detachable vaso-occlusive devices may be found in U.S. Pat. Nos. 5,122,136 and 5,354,295, each to Guglielmi et al. In these devices, the vaso-occlusive portion of the assembly is attached to a pusher via a small, electrolytically severable joint. The electrolytically severable joint is severed by the placement of an appropriate voltage on the core wire. The joint erodes in preference either to the vaso-occlusive device itself or to the pusher core wire. The core wire is often simply insulated to prevent the electrolytic response caused by the imposition of electrical current.

Further improvement upon the electrolytical detachment mechanism described just is found in U.S. patent application Ser. No. 08/205,512, filed Mar. 3, 1994, for "IMPLANT DETACHMENT DETECTION SYSTEM AND METHOD FOR DETECTING SEPARATION OF VASO-OCCLUSIVE DEVICES". This document described a procedure for superimposing a modest alternating current upon the direct current signal. A sensing circuit monitors the alternating current as an indicator of the progression of coil detachment.

Improvements in enhancing the thrombogenic or other occlusive tissue response to metal coils has also been disclosed. For example, vaso-occlusive coils having fibers attached thereto are known—see, for example, U.S. Pat. No. 5,226,911, to Chee et al.

Each of the devices described above may be used in the treatment by occlusion of aneurysms. As noted above, aneurysms present particularly acute medical risk due to the dangers of potential rupture of the thin wall inherent in such aneurysm. Occlusion of aneurysms by use of vaso-occlusive coils without occluding the adjacent artery is a special challenge and is a desirable method of reducing such risk of rupture.

As noted above, the use of vaso-occlusive coils in treating aneurysms is widespread. These vaso-occlusive devices are placed in an aneurysm in the following fashion. A microcatheter is initially steered into or adjacent to the entrance of an aneurysm, typically aided by the use of a steerable guidewire. The wire is then withdrawn from the microcatheter lumen and replaced by the vaso-occlusive coil. The vaso-occlusive coil is advanced through and out of the microcatheter, desirably being completely delivered into the aneurysm. After, or perhaps, during, delivery of such a coil into the aneurysm, there is a specific risk that a portion of the coil might migrate out of the aneurysm entrance zone and into the feeding vessel. The presence of such a coil in that feeding vessel may cause the highly undesirable response of causing an occlusion there. Also, there is a quantifiable risk that the blood flow in the vessel and aneurysm may induce movement of the coil farther out of the aneurysm, resulting in a more developed embolus in the patent vessel.

One type of aneurysm, commonly known as a "wide neck aneurysm" is known to present particular difficulty in the placement and retention of vaso-occlusive coils. Wide neck aneurysms are herein referred to as aneurysms of vessel walls having a neck or a "entrance zone" from the adjacent vessel, which entrance zone has a diameter that either: (1) is at least 80% of the largest diameter of the aneurysm; or (2) is clinically observed to be too wide effectively to retain vaso-occlusive coils that are deployed using the techniques discussed above.

Furthermore, vaso-occlusive coils lacking substantial secondary shape strength may be difficult to maintain in position within an aneurysm no matter how skillfully they are placed.

There are few disclosed devices for maintaining the presence of vaso-occlusive coils within an aneurysm. One such device is shown in U.S. patent application Ser. No. 08/690,183, filed Jul. 26, 1996, for "ANEURYSM CLOSURE DEVICE ASSEMBLY" (attorney docket 29025-20162.00). That application describes devices which are said to be placed within the lumen of a feed vessel exterior to the aneurysm so to retain coils within the aneurysm cavity. That is to say that the retainer device is released in the good vessel exterior to the aneurysm. The device is held in place via the use of radial pressure on the vessel wall. After the device is released and set in an appropriate place, a microcatheter is inserted into the lumen behind the retainer device; the distal end of the catheter is inserted into the aneurysm cavity. One or more vaso-occlusive devices is introduced into the aneurysm cavity. The retainer device maintains the presence of those vasoocclusive devices within the aneurysm no matter whether the aneurysm is a large mouth aneurysm or not.

Another device for closing an aneurysm is found in U.S. patent application Ser. No. 08/588,195 filed Jan. 18, 1996, for "ANEURYSM CLOSURE METHOD" (attorney docket number 29025-20136.00). In this procedure, a vaso-occlusive device such as a coil or braid has on its outer surface a polymeric composition which may be reformed or solidified in situ within the human body. The device is simply inserted into the aneurysm and the polymer is then reformed, e.g., by the application of light to melt or otherwise reform the polymer exterior to the vaso-occlusive device. The vaso-occlusive device then sticks to itself at the various sites of self-contact and forms a rigid whole mass within the aneurysm.

There are a variety of other vaso-occlusive coils and devices which may be specified herein. The material provided above is only exemplary of the patents and publications dealing with such devices. No coil retainer device of the structure described herein is seen in any of the references described above.

SUMMARY OF THE INVENTION

This invention includes an implantable medical device useful for retaining other occlusion device at an occlusion site, such as an aneurysm, and related methods of introducing and installing that implantable retainer at the occlusion site. Combinations of the retainer device and its included vaso-occlusive material or device are also an aspect of the invention as are combinations of the retainer device and its delivery components. In particular, the invention involves an implantable retainer which is deliverable through an elongated tubular delivery device such as a vascular catheter. The assemblage includes an implantable retainer which is placed in and allowed to remain in an aneurysm and a tubular delivery member to which it is attached by an electrolytically severable joint. In general, the implantable retainer component may either extend from the distal end of the tubular delivery member or may include a small tubular section which in turn is slipped over the distal end of the delivery component.

The joint itself is electrolytically severable upon application of a suitable current to the joint, typically by use of a conductor wire which may be placed in the wall of the delivery member. The joint is comparatively more electrolytically dissolvable when a current is applied than are any of the rest of the components which surround or deliver it. The retainer component itself has a number of array elements shaped preferably the general shape of flower petals in a flower. The array elements may either be exterior wires or regions having exterior wires and covered with a mesh of some kind. The petals or array elements have a primary shape when inside the delivery tubular member and then assume a secondary shape upon exit from the distal end of that delivery tubular member. Once the retainer subassembly containing the array elements is in place, the vaso-occlusive device, e.g. vaso-occlusive coils, may be introduced into the aneurysm either through the small tubular member to which the array members are attached or, if the array members do not have a mesh covering, through the open area found at the neck of the aneurysm.

DESCRIPTION OF THE INVENTION

This invention relates to a device and a procedure for stabilizing the position and, usually, the structure of vaso-occlusive devices which are placed in a target occlusion site, usually an aneurysm. The retaining devices prevent the potential migration of those one or more occlusive devices (e.g., helically wound coils) from that target occlusion site, by forming a barrier at the entrance zone to the aneurysm where it meets a feeding vessel.

Figure 1:
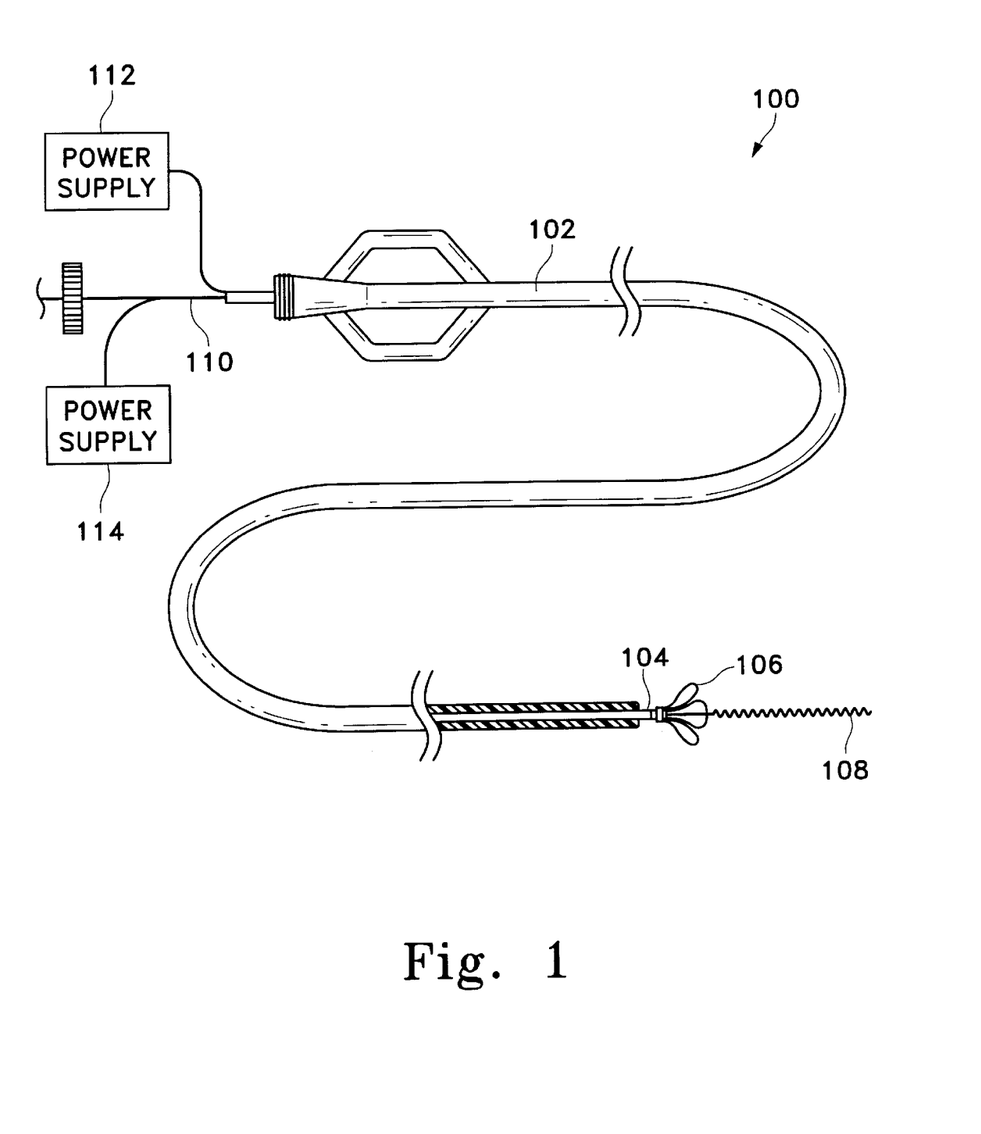
FIG. 1 shows partial, cross sectional, plan view of a delivery device, aneurysm retainer, vaso-occlusive device, and respective power supplies all made in accordance with the invention.

FIG. 1 shows in partial cross section, the general assemblage of components used to deliver both the aneurysm neck bridge made according to this invention and the accompanying vaso-occlusive devices. Specifically, FIG. 1 shows a tubular delivery member (102), which may be vascular catheter designed for other purposes or more likely one specifically designed for this purpose. Interior to the delivery catheter or member (102) is an inner elongated tubular member (104), which is attached via an electrlytically severable joint to the aneurysm neck bridge (106). The severable joint is of a scale that cannot easily be seen in FIG. 1 and is depicted in greater clarity in FIGS. 2A and 2B. A vaso-occlusive device, in this case a helically wound coil (108) is interior to both of the tubular delivery members and it too is severable from its delivery member by an electrolytically severable joint which also is to small to be seen in this particular rendition. The core wire (110) to which it is attached may more clearly be seen at the proximal end of the overall assembly (100). It will be noted at proximal end of the delivery catheter (102) that a pair of power supplies are depicted. Schematically at least, a first power supply (112) is used to deliver current to the electrolytically severable joint, the severance of which releases the aneurysm neck bridge (106). A second power supply (114) is depicted as providing a current to sever the electrolytic joint attached to vaso-occlusive coil (108). It would not be typical that both power supplies are used at the same time and consequently a single power supply is likely adequate for both purposes obviously after having switched from one conductor to the other.

Figure 2A:
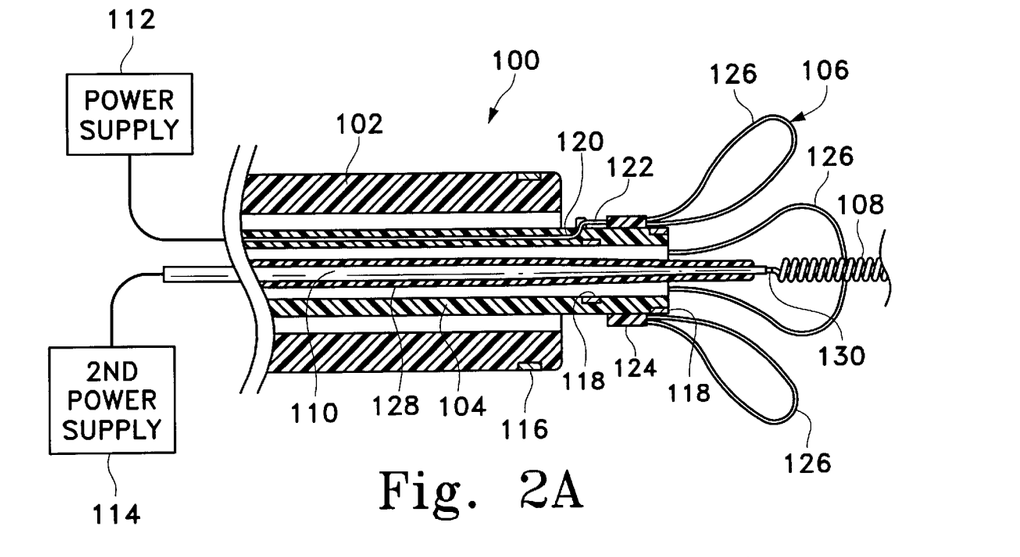
FIG. 2A shows a cross section of the distal tip of the device depicted in FIG. 1.

The aneurysm neck bridge (106) is shown in FIGS. 1 and 2A in the so-called "secondary" shape or condition. The neck bridge or retainer (106) is delivered to the chosen site within the lumen of the delivery catheter (102). It is only after the retainer (106) is pushed from the distal end of the delivery catheter (102) that it unfolds to form the secondary shape shown in these two drawings. Obviously, prior to the time it is pushed from the safe harbor within the delivery catheter (102), it generally maintains the shape of the inner lumen of that catheter (102). Consequently, we describe the shape of the aneurysm retainer (106) as a "secondary shape" which is different from the "primary shape" or "delivery shape" it maintains during the time the neck bridge (106) is within the delivery catheter (102).

FIG. 2A is a close-up cross section of the distal tip of the assembly (100) shown in FIG. 1. The distal tip of delivery catheter (102) may be seen with its radio-opaque marker (116). The inner tubular delivery member (104) may be seen in cross section. Inner delivery tubular member (104) is shown with two radio-opaque markers (118). Conductor (120) is for conducting current from first power supply (112) to electrolytically detachable joint (122). The construction of electrolytically severable joint (122) is shown in more detail elsewhere herein. Aneurysm neck bridge (106) is shown in this variation as having a small tubular member (124), the interior of which is slid onto the distal end of inner delivery of tubular member (104). The fit of this small tubular member (124) is typically somewhat loose around the inner delivery member (104) and is maintained in position on that inner delivery member (104) by the electrolytic joint (122). Finally, on retainer member (106) may be seen a number of array members or wires (126) which, upon placement in the aneurysm, spread to the general shape shown in FIG. 2A.

Finally, in FIG. 2A, core wire (110) may be seen, along with its insulating layer (128). This insulating layer (128) allows the current flowing from second power supply (114) to pass without creating other circuits, to the electrolytically severable joint (130). Passage of current through electrolytically severable joint (130) and its ultimate severance from core wire (110) will release vaso-occlusive device (108) into the aneurysm. The sequence of operation of each of these devices will be apparent from the discussion below.

Figure 2B:
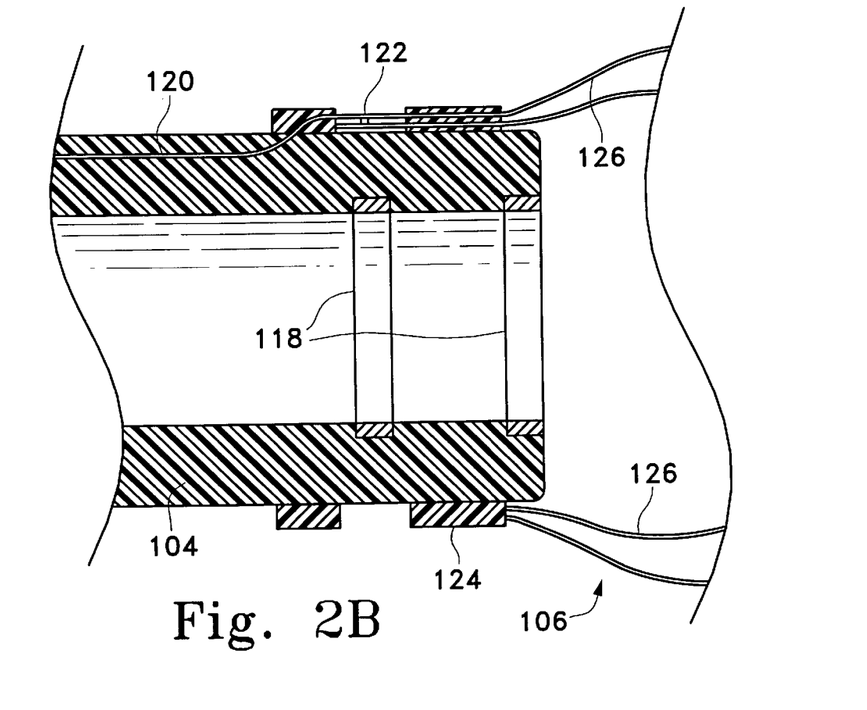
FIG. 2B shows a close up, cross sectional view of a portion of the delivery device showing one variation of the electrolytically detachable joint suitable for use in this invention.

FIG. 2B shows an even greater magnification (also in cross section) of the most distal portion of inner tubular delivery member (104). The radio-opaque members (118) are also shown in FIG. 2B. The small tubular member (124) forming the central portion of retainer member (106) may also be seen. Of special importance are the conductor wire (120) and the electrolytic joint (122). A portion of array members (126) may also be seen in FIG. 2B.

Figure 3:
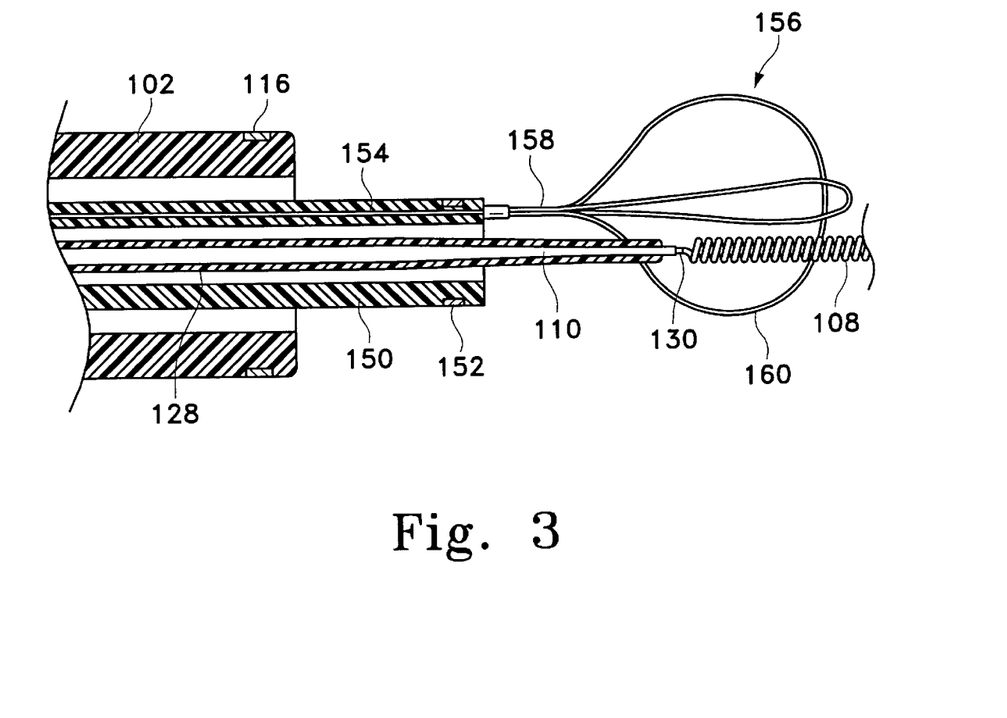
FIG. 3 shows a close-up, cross sectional view of a variation of the invention in which the retainer device is included on the distal tip of the delivery tubular member.

FIG. 3 shows a cross-sectional view of another variation of the inventive concept described herein. By way of summary, the major difference between the variation shown in FIG. 3 and the variation shown in FIGS. 2A and 2B involves the manner in which the retainer or neck bridge is attached to the elongate tubular delivery member.

FIG. 3 again shows a delivery catheter (102) with its radio-opaque marker (116). The inner elongate delivery member (150) also has one or more radio-opaque markers (152) and conductive wire (154) which may be embedded in the member wall. The major difference from the previously described variations of the invention is that the aneurysm bridge or retainer subassembly (156), although attached with an electrolytically severable joint (158) to delivery member (150), is so attached without benefit of the short tubular member 124 (shown in FIGS. 2A and 2B). Instead, the electrolytic joint (158) fixedly attaches the retainer subassembly (156) to the distal end of delivery member (150). A simple pair of loops (160) are shown as making up aneurysm neck bridge or retainer (156) subassembly. This configuration or that shown in the drawings which follow may be used as desired.

Finally, core wire (110) with its insulative coating (128) is shown also having an electrolytically severable joint (130) and a vaso-occlusive coil (108).

The array elements or loops (126) variously in FIGS. 2A and 2B and (156) in FIG. 3 and those discussed below, are required to undertake massive changes in shape during deployment in the human body. To undertake such stress, it is usually preferable that the various retainer subassembly elements be produced of a material such as a super-elastic alloy. Super-elastic or pseudoelastic shape recovery alloys are well known in this art. For instance, U.S. Pat. Nos. 3,174,851; 3,351,463; and 3,753,700 each describe one of the more well known super-elastic alloys, known as Nitinol. These alloys are characterized by their ability to be transformed from an austenitic crystal structure to a stress-induced martensitic (SIM) structure at certain temperatures and then to return elastically to the austenitic shape when the stress is removed. These alternating crystal structures provide the alloy with its super-elastic properties. The alloy mentioned in the three patents just above, is a nickel titanium alloy. It is readily commercially available and undergoes the austenitic-SIM-austenitic transformation at a variety of temperatures between −20° C. and +30° C.

These alloys are especially suitable because of their capacity to recover elastically, almost completely, to the initial configuration once the stress is removed. Typically in services such as are described here there is little permanent plastic deformation, even at relatively high strains. This ability allows the retainer device to undertake substantial bends both as it is collapsed to enter the various tubular delivery devices and as it undertakes further bending in passing through the vasculature. In spite of this bending, it returns to its original shape once the bend has been traversed without retaining kinks or permanent bends.

Of the super-elastic alloys currently available, we consider our preferred material to be nominally 50.6±2% nickel with most of the remainder being titanium. Up to about 5% of the alloy may be a member of the iron group of metals, particularly chromium and iron. The alloy should not contain more than about 500 parts per million of oxygen, carbon, or nitrogen. The transition temperature of this material is not particularly important, but it should be reasonably below the typical temperature of the human body so to allow it to be in its austenitic phase during use. The diameter of the wires or ribbons making up the various array elements preferably are smaller than about 0.010 inches in diameter. These super-elastic alloys are not always completely visible under fluoroscopy as it is used in the human body. Consequently it may be desirable to add a covering of some kind to improve the radio-opacity of the device. Radio-opaque metals such as gold and platinum are well known. They may be added the various elements of this inventive device by such widely recognized methods as by plating or by wrapping the element in a radio-opaque wire or ribbon.

Although we have discussed producing these devices from super-elastic alloys, other metals may in certain circumstances be appropriate. Such metals include a number of the stainless steels and other highly elastic, if not super-elastic alloys. Furthermore, it is within the scope of this invention that the various array elements be of polymeric materials. Polymeric materials are somewhat easier to work with in forming a device. Such polymeric materials may include members from the group of polyethylene, polypropylene, polytetraflouroethylene, various Nylons, and the like. These polymers are easily chosen by one having ordinary skill in this art for the purposes shown herein.

The various electrolytically severable joints (122 in FIGS. 2A and 2B and 130 in FIGS. 2A and 3, and 158 in FIG. 3) may also be denominated as sacrificial links. The core wire (110) is typically coated with an electrical insulator which is not susceptible to dissolution via the electrolysis process in blood or other ionic media. Suitable coatings for core wires (110) includes such insulating materials as the polyfluorocarbons (e.g., Teflon), polyurethane, polyethylene, polypropylene, polyimides, or other suitable well known polymeric materials. The various electrolytically severable joints are not coated with such an insulator but they are made of materials which are susceptible to electrolytic dissolution in blood. These electrolytically severable joints may be a simple uninsulated continuation of, e.g., the stainless steel core wire (110), which has been insulated proximally of the joint. It should also be apparent that the sacrificial joints are more susceptible to electrolysis than any of the other elements of the device near that joint. Further discussion of the construction of, placement of, and other physical details of such electrolytically severable joints may be found in U.S. Pat. Nos. 5,122,136 to Guglielmi et al.; 5,354,295 to Guglielmi et al.; and 5,624,449 to Pham et al.; and others.

Figure 4A:
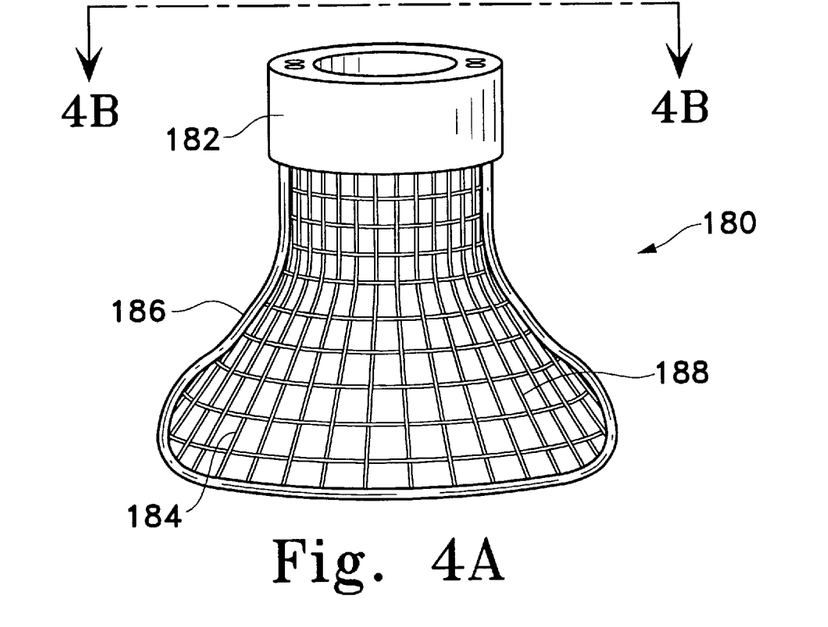
FIGS. 4A and 4B show, respectively, side and top views of one variation of the aneurysm retainer made according to this invention.
Figure 4B:
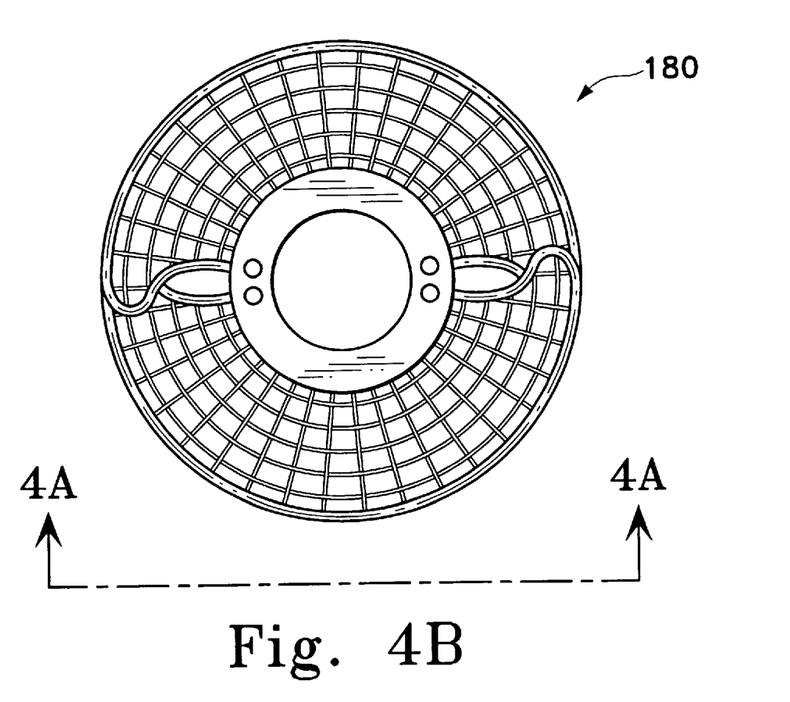

FIGS. 4A and 4B show respectively a side, top view of another variation (180) the inventive retainer. This retainer includes the small tubular member (182) which, after being placed in an aneurysm, is near the mouth of the aneurysm. This variation (180) has two array elements (184). Each of the portrayed array elements (184) includes an outer wire or ribbon rim (186) and a mesh filler (188). The mesh filler (188) may be a woven cloth, a flat woven mesh, a knitted mesh, or other common and non-critical sheetings. Although the rim material (186) is preferably of a form which retains a large measure of elasticity after having been bent, the filler or field material (188) need not be so elastic. Indeed it is preferable that the material making up sheeting (188) not have substantial strength so to allow the device to be folded and placed into the various delivery catheters and the like discussed above without adding unnecessary stiffness. The sole function of the sheeting (188) is simply to maintain the presence of the vaso-occlusive coils in the aneurysm. It is the rim material (186) of the array member (184) which is intended to maintain the structural integrity of the device as it is situated in the aneurysm.

Figure 5A:
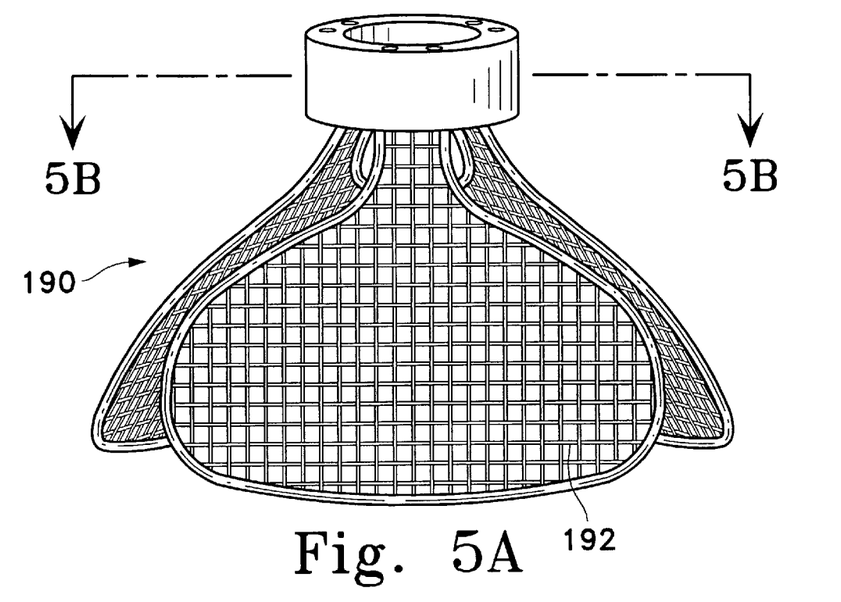
FIGS. 5A and 5B show, respectively, a second variation of the invention made according to this invention.
Figure 5B:
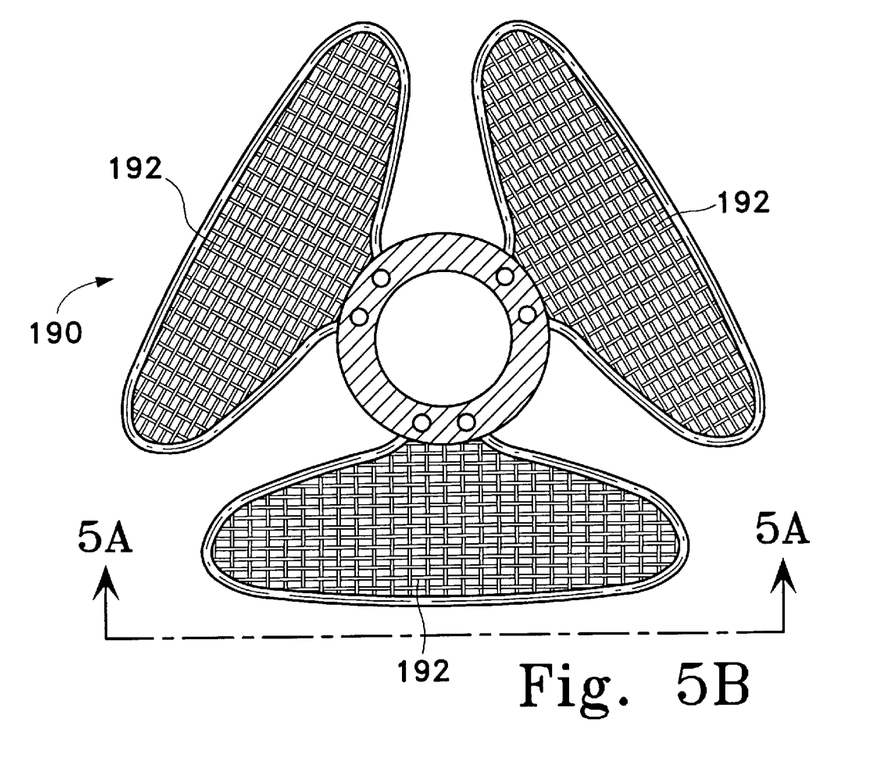

FIG. 5A and FIG. 5B show respectively side and top views of aneurysm retainer subassemblies (190) made according to the invention. This variation (190) is similar to that shown in FIGS. 4A and 4B except that it has three array elements (192) rather than the two overlapping elements shown in FIGS. 4A and 4B. This configuration has benefit of being somewhat more open and perhaps allowing easier access to the interior of the aneurysm for placement of vaso-occlusive materials including coils and chemical vaso-occlusive materials such as cyanoacrylates. Materials of construction in the variation shown in FIGS. 5A and 5B are the same as those utilized in FIGS. 4A and 4B.

Figure 6:
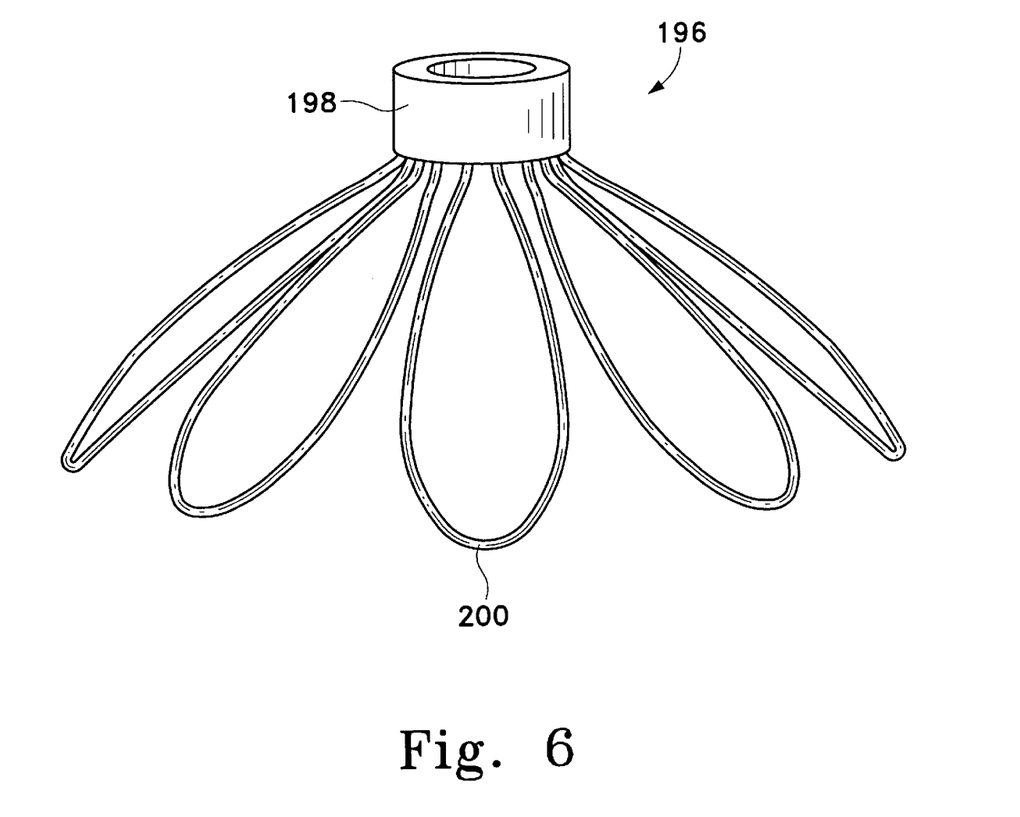
FIG. 6 shows, in side view, a variation of the aneurysm retainer made according to this invention.

FIG. 6 shows another variation (196) of the inventive aneurysm retainer assembly. It too includes a small tubular member (198) which, as with variations discussed above, become situated at the mouth of the aneurysm, but preferably not in the feed vessel, and is the principal passageway for entry of vaso-occlusive devices into the aneurysm cavity. This variation of the invention includes a number of interior array elements (200). In FIG. 6, the array elements (200) are shown without the presence of a mesh or other covering in the loops of the array element (200). It is within the scope of this invention that array elements (200) and the analogous ones shown above may be used with or without mesh depending upon the shape of the aneurysm and the configuration of its opening into the feed vessel.

For instance, it may be highly desirable to use array elements having mesh coverings. This mesh would provide additional stability to the large mouth of an aneurysm and therefore the lessen the chance that vaso-occlusive device placed in the aneurysm will either enter the feed vessel or creep distally with blood flow.

Figure 7A:
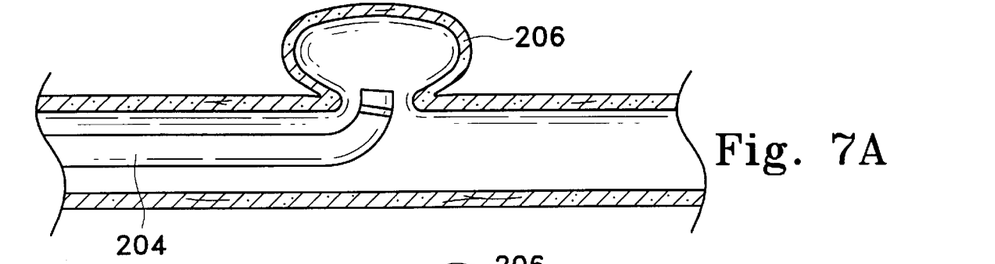
FIGS. 7A–7E show a procedure for introducing the aneurysm retainer made according to this invention and its allied vaso-occlusive device into the target aneurysm.
Figure 7B:
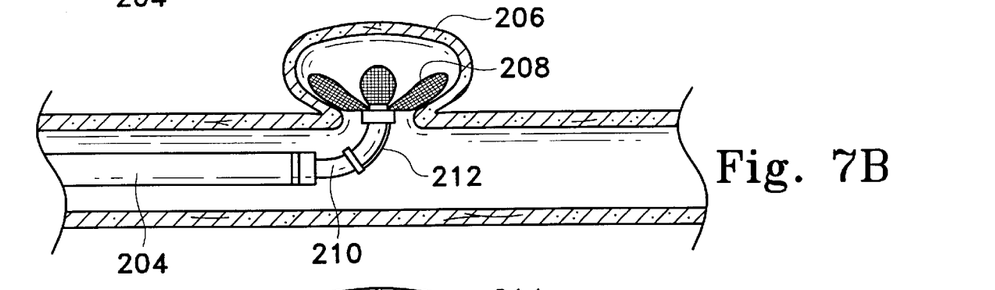
Figure 7C:
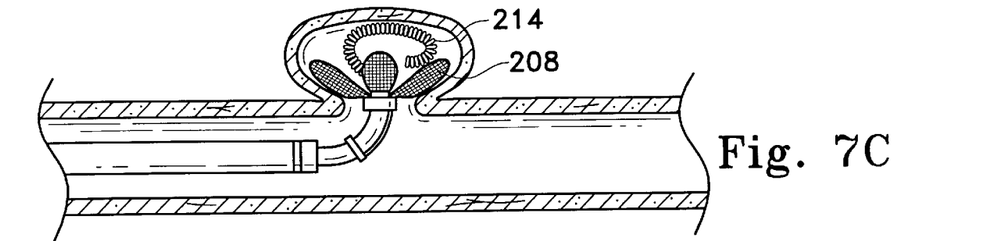

FIGS. 7A through 7E show the manner in which these devices are typically used in occluding and stabilizing an aneurysm. FIG. 7A shows the placement of the distal end of a catheter (204) within the mouth of an aneurysm (206). FIG. 7B shows catheter (204) having been withdrawn proximally a bit and the aneurysm retainer device (208) placed in the mouth of the aneurysm (206). The inner tubular delivery member (210) is shown with its electrolytic joint (212) still intact. FIG. 7C shows the introduction of vaso-occlusive devices, in this case helically wound coils (214) into the vascular cavity interior to the retainer device (208).

Figure 7D:
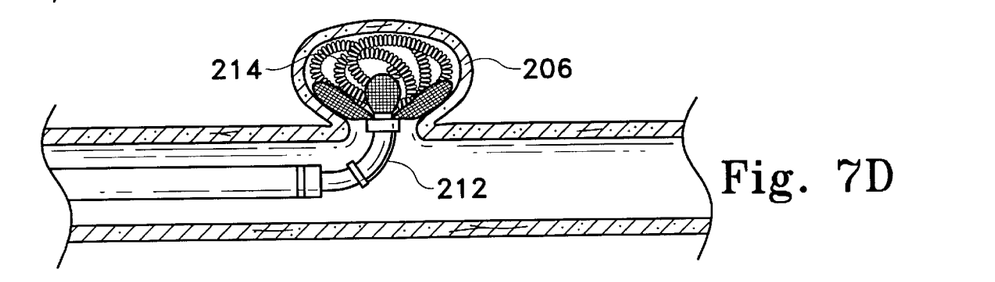
Figure 7E:
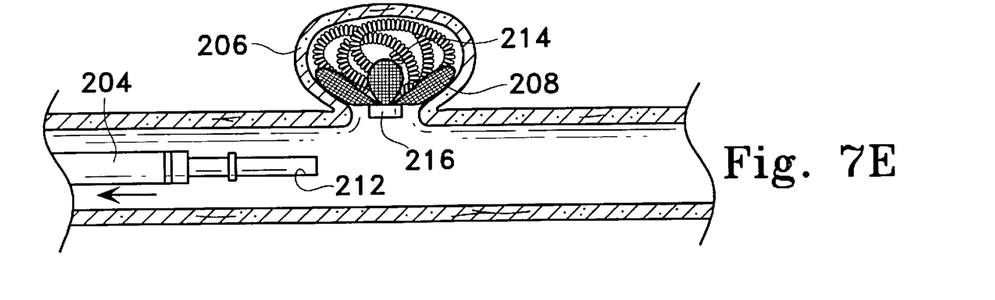

FIG. 7D shows the vascular cavity of aneurysm (206) filled with coils (214) and the electrolytic joint maintaining the continuity between the core wire (shown in other drawings) severed. In FIG. 7E, electrolytic joint (212) has been severed and the placement catheter (204) and the interior tubular delivery member (212) have withdrawn leaving the vaso-occlusive device (214) in place within aneurysm (206). The neck bridge or retainer (208) is shown stabilizing the presence of that coil (214) and preventing vaso-occlusive coil (214) from being drawn into the feed vessel. It should be noted that this variation of the invention shows that the small tubular member (216) is also placed well out of the normal blood flow of the feed vessel.

Many alterations and modifications may be made by those of ordinary skill in this art, without departing from the spirit and scope of this invention. The illustrated embodiments have been shown only for purposes of clarity and the examples should not be taken as limiting the invention as defined in the following claims. Which claims are intended to include all equivalents, whether now or later devised.

I claim as my invention:

1. A retainer assembly deliverable through a vascular catheter comprising:

a.) an elongated tubular delivery member having a proximal end and a distal end, b.) a vaso-occlusion device retainer subassembly comprising a central tubular section, a plurality of loops having ends fixedly attached to said central tubular section, said retainer subassembly having a first delivery shape when within said vascular catheter and a second deployed shape, different than the first delivery shape, when said retainer subassembly is not retained within said vascular catheter, said central tubular section slidably and removably positioned coaxially about and adjacent the distal end of said elongated tubular delivery member, said central tubular section being slidable along said elongated tubular delivery member upon severance of an electrolytic joint, and c.) said electrolytically severable joint between said retainer subassembly and said elongated tubular delivery member, severable upon application of a suitable current to said joint.

2. The retainer assembly of claim 1 wherein said plurality of loops are constructed of a material selected from the group consisting of stainless steels and super-elastic alloys.

3. The retainer assembly of claim 1 wherein said plurality of loops are at least partially covered with a fabric or mesh.

4. The retainer assembly of claim 1 wherein the said plurality of loops are radio-opaque.

5. The retainer assembly of claim 1 wherein said elongated tubular delivery member additionally comprises at least one radio-opaque marker located distally.

6. The retainer assembly of claim 1 wherein said elongated tubular delivery member has a lumen from said proximal end to said distal end and wherein said lumen contains a vaso-occlusive device delivery member comprising in combination a.) a core wire having a proximal end and a distal end, said core wire distal end severably attached to an electrolytically severable joint, which severable joint is severable upon application of a suitable current, b.) said electrolytically severable joint, and c.) a vaso-occlusive device fixedly attached to said electrolytically severable joint, which vaso-occlusive device is released from said core wire upon severance of said electrolytically severable joint.

7. The retainer assembly of claim 1 further comprising said vascular catheter.

8. A retainer assembly deliverable through a vascular catheter comprising:

a.) an elongated tubular delivery member having a proximal end and a distal end, b.) a vaso-occlusive device retainer subassembly comprising a plurality of loops fixedly attached to a distal end of an electrolytically severable joint, the proximal end of which electrolytically severable joint is fixedly attached to the distal end of said elongated tubular delivery member, said retainer subassembly having a first delivery shape when within said vascular catheter and a second deployed shape, different from the first delivery shape, when said retainer subassembly is not retained within said vascular catheter, and c.) said electrolytically severable joint between said retainer subassembly and the distal end of said elongated tubular delivery member, severable upon application of a suitable current to said joint.

9. The retainer assembly of claim 8 wherein said plurality of loops are constructed of a material selected from the group consisting of stainless steels and super-elastic alloys.

10. The retainer assembly of claim 8 wherein said plurality of loops are at least partially covered with a fabric or mesh.

11. The retainer assembly of claim 8 wherein the said plurality of loops are radio-opaque.

12. The retainer assembly of claim 8 wherein said elongated tubular delivery member additionally comprises at least one radio-opaque marker located distally.

13. The retainer assembly of claim 8 wherein said elongated tubular delivery member has a lumen from said proximal end to said distal end and wherein said lumen contains a vaso-occlusive device delivery member comprising in combination a.) a core wire having a proximal end and a distal end, said core wire distal end severably attached to an electrolytically severable joint, which severable joint is severable upon application of a suitable current, b.) said electrolytically severable joint, and c.) a vaso-occlusive device fixedly attached to said electrolytically severable joint, which vaso-occlusive device is released from said core wire upon severance of said electrolytically severable joint.

14. The retainer assembly of claim 8 further comprising said vascular catheter.

\* \* \* \* \*